US00PP18087P2

(12) United States Plant Patent
Hartman

(10) Patent No.: US PP18,087 P2
(45) Date of Patent: Sep. 25, 2007

(54) *CALADIUM* PLANT NAMED 'VICTORIA'

(50) Latin Name: *Caladium×hortulanum*
Varietal Denomination: Victoria

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 11/415,477

(22) Filed: May 1, 2006

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent Bell
(74) *Attorney, Agent, or Firm*—C. A. Whealy

(57) ABSTRACT

A new and distinct cultivar of *Caladium* plant named 'Victoria', characterized by its compact, symmetrical, upright, outwardly arching and rounded plant habit; dense and bushy growth habit; undulate strap-like leaves that are rugose giving a highly textured appearance; and red, pink and green-colored leaves.

3 Drawing Sheets

Botanical designation: *Caladium×hortulanum.*
Cultivar denomination: 'Victoria'.

BACKGROUND OF THE INVENTION

The present invention relates to a new and distinct cultivar of *Caladium* plant, botanically known as *Caladium× hortulanum,* commercially referred to as a strap-leaf *Caladium* and hereinafter referred to by the name 'Victoria'.

The new *Caladium* is a naturally-occurring whole plant mutation of the *Caladium×hortulanum* cultivar Florida Sweetheart, disclosed in U.S. Plant Pat. No. 8,526. The new *Caladium* was discovered and selected by the Inventor in a controlled environment in Lake Placid, Fla. on Jun. 15, 2002 from within a population of plants of the cultivar Florida Sweetheart. The new *Caladium* was selected on the basis of its unique leaf texture and coloration.

Asexual reproduction of the new cultivar by tuber divisions in a controlled environment in Lake Placid, Fla. since Apr. 15, 2003 has shown that the unique features of this new *Caladium* are stable and reproduced true to type in successive generations of asexual reproduction.

SUMMARY OF THE INVENTION

The cultivar Victoria has not been observed under all possible environmental conditions. The phenotype may vary somewhat with variations in environment such as temperature and light intensity, without, however, any variance in genotype.

The following traits have been repeatedly observed and are determined to be the unique characteristics of 'Victoria'. These characteristics in combination distinguish 'Victoria' as a new and distinct cultivar of *Caladium:*

1. Compact, symmetrical, upright, outwardly arching and rounded plant habit.
2. Dense and bushy growth habit.
3. Undulate strap-like leaves that are rugose giving a highly textured appearance.
4. Red, pink and green-colored leaves.

In side-by-side comparisons conducted in Lake Placid, Fla., plants of the new *Caladium* differed from plants of the parent, the cultivar Florida Sweetheart, in the following characteristics:

1. Plants of the new *Caladium* were more compact than and not as vigorous as plants of the cultivar Florida Sweetheart.
2. Leaves of plants of the new *Caladium* were more undulate than leaves of plants of the cultivar Florida Sweetheart.
3. Leaves of plants of the new *Caladium* were more rugose and more textured in appearance than leaves of plants of the cultivar Florida Sweetheart.
4. Under high light conditions, plants of the new *Caladium* had darker red-colored leaves than plants of the cultivar Florida Sweetheart.
5. Plants of the new *Caladium* had shorter leaf petioles than plants of the cultivar Florida Sweetheart.

Plants of the new *Caladium* can be compared to plants of the *Caladium* cultivar Florida Red Ruffles, disclosed in U.S. Plant Pat. No. 13,136. In side-by-side comparisons conducted in Lake Placid, Fla., plants of the new *Caladium* differed from plants of the cultivar Florida Red Ruffles in the following characteristics:

1. Plants of the new *Caladium* were larger than plants of the cultivar Florida Red Ruffles.
2. Leaves of plants of the new *Caladium* were more undulate than leaves of plants of the cultivar Florida Red Ruffles.
3. Leaves of plants of the new *Caladium* were more rugose and more textured in appearance than leaves of plants of the cultivar Florida Red Ruffles.
4. Plants of the new *Caladium* and of the cultivar Florida Red Ruffles differed in leaf coloration.
5. Plants of the new *Caladium* had lighter-colored leaf petioles than plants of the cultivar Florida Red Ruffles.

Plants of the new *Caladium* can be compared to plants of the *Caladium* cultivar Lance Whorton, not patented. In side-by-side comparisons conducted in Lake Placid, Fla., plants of the new *Caladium* differed from plants of the cultivar Lance Whorton in the following characteristics:

1. Plants of the new *Caladium* were more compact than plants of the cultivar Lance Whorton.

2. Leaves of plants of the new *Caladium* were more undulate than leaves of plants of the cultivar Lance Whorton.
3. Leaves of plants of the new *Caladium* were more rugose and more textured in appearance than leaves of plants of the cultivar Lance Whorton.
4. Plants of the new *Caladium* and of the cultivar Lance Whorton differed in leaf coloration.
5. Plants of the new *Caladium* had lighter-colored leaf petioles than plants of the cultivar Lance Whorton.

BRIEF DESCRIPTION OF THE PHOTOGRAPHS

The accompanying photographs illustrate the overall appearance of the new *Caladium*. These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet comprises a side perspective view of a typical plant of 'Victoria' grown in a container.

The photograph on the second sheet comprises a side perspective view of typical plants of 'Florida Sweetheart' (left) and 'Victoria' (right) grown in containers.

The photographs on the third sheet comprise top perspective views of typical plants of 'Florida Sweetheart' (bottom) and 'Victoria' (top) grown in ground beds in an outdoor nursery.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in 15-cm containers in Lake Placid, Fla. during the spring in a polyethylene-covered shadehouse and under conditions and practices which approximate those generally used in commercial *Caladium* production. During the production of the plants, day temperatures ranged from about 21° C. to 38° C., night temperatures ranged from about 10° C. to 21° C. and light levels about 8,000 foot-candles. Plants were about seven weeks from planting tubers when the photographs and the detailed description were taken.

Botanical classification: *Caladium×hortulanum* cultivar Victoria.

Parentage: Naturally-occurring whole plant mutation of the *Caladium×hortulanum* cultivar Florida Sweetheart, disclosed in U.S. Plant Pat. No. 8,526.

Propagation:

*Type.*—By tuber divisions.

*Time to initiate roots, summer.*—About seven to ten days at 32° C.

*Time to initiate roots, winter.*—About two to three weeks at 24° C.

*Tuber description.*—Number of buds per tuber: About eight actively growing buds/shoots and about ten dormant buds. Height: About 2.8 cm. Diameter: About 4 cm. Texture: Thick, starchy; somewhat brittle. Color: Epidermis, 200A; interior, 11B to 11C. Root description/habit: Dense, thick and white fleshy roots with finer lateral roots.

Plant description:

*Plant/growth habit.*—Compact, upright, outwardly arching and rounded plant habit. Densely-foliated; vigorous, dense and bushy growth habit; suitable for 10-cm to 25-cm containers. Mostly upright leaf petioles.

*Plant height.*—About 19 cm from soil level to top of leaf plane.

*Plant spread.*—About 42 cm.

*Cataphylls.*—Length: About 2.5 cm. Width: About 9 mm. Shape: Linear to elliptic. Apex: Acuminate. Base: Sheathing the stem. Color, outer surface: N170D; stripes and streaks, N186B to N186C. Color, inner surface: N170D to 155A; faint streaks, N186C.

Foliage description:

*Length.*—About 14 cm.

*Width.*—About 9 cm.

*Shape.*—Ovate to lanceolate.

*Apex.*—Acuminate to acute.

*Base.*—Sagittate to cordate.

*Margin.*—Entire; distinctly undulate.

*Texture, upper surface.*—Smooth, glabrous; rugose giving a highly textured appearance.

*Texture, lower surface.*—Smooth, glabrous; glaucous; rugose giving a highly texture appearance.

*Venation pattern.*—Pinnate.

*Color.*—Developing leaves, upper surface: Margins: 147A. Center: Intervenal areas, 195B to 195C tinged with 137A, often flushed overall with 185C to 185D. Areas of 185C follow the veins. Venation: 187B to 187C; peripheral marginal veins, 147A tinged with 187C; at the petiole attachment, 187B to 59A; midrib, 187B. Notch: 59A. Developing leaves, lower surface: Margins: 137A to 147A. Center: Intervenal areas, 195B tinged with 147B to 147C tinged with 191A. Areas of 185C to 185D follow the veins. Venation: 147A to 147B; at the petiole attachment, 184B to 184C; midrib, 185B to 185C. Notch: 184B to 184C tinged with 191A. Fully developed leaves, upper surface: Margins: Darker and more green than 147A. Center: Intervenal areas, 195B tinged with 137A, often flushed overall with 185C to 184C. Areas of 184B to 184C follow the veins. Venation: 187B to 187C; peripheral marginal veins, 147A tinged with 187B to 187C; at the petiole attachment, 59A to 187B; midrib, 187B. Notch: 59A. Fully developed leaves, lower surface: Margins: 191A. Center: Intervenal areas, 195B tinged with 147B. Areas of 185B to 185C follow the veins. Venation: 147A to 147B; the petiole attachment, 184B to 184C; midrib, 147A to 147B tinged with 185C. Notch: 184B to 184C.

*Petiole.*—Aspect: Mostly erect, outwardly arching with development. Length: About 13 cm. Diameter, distal: About 3 mm. Diameter, proximal: About 5 mm. Strength: Strong; flexible. Color: N170D; stripes and streaks, N186B to N186C. Wing length: About 3 cm. Wing depth: About 6 mm. Wing color, outer surface: N170D; stripes and streaks, N186B to N186C. Wing color, inner surface: N170D to 155D; faint streaks, N186C.

Flower description: Flower development has not been observed on plants of the new *Caladium*.

Disease/pest resistance: Plants of the new *Caladium* have not been observed to be resistant to pathogens or pests common to *Caladium*.

Temperature/weather tolerance: Plants of the new *Caladium* have been observed to be tolerant to temperatures ranging from about 7° C. to about 40° C. Plants of the new *Caladium* have been observed to be tolerant to rain and wind. Plants of the new *Caladium* will tolerate full sun conditions in Florida without leaf scorching.

It is claimed:

1. A new and distinct *Caladium* plant named 'Victoria' as illustrated and described.

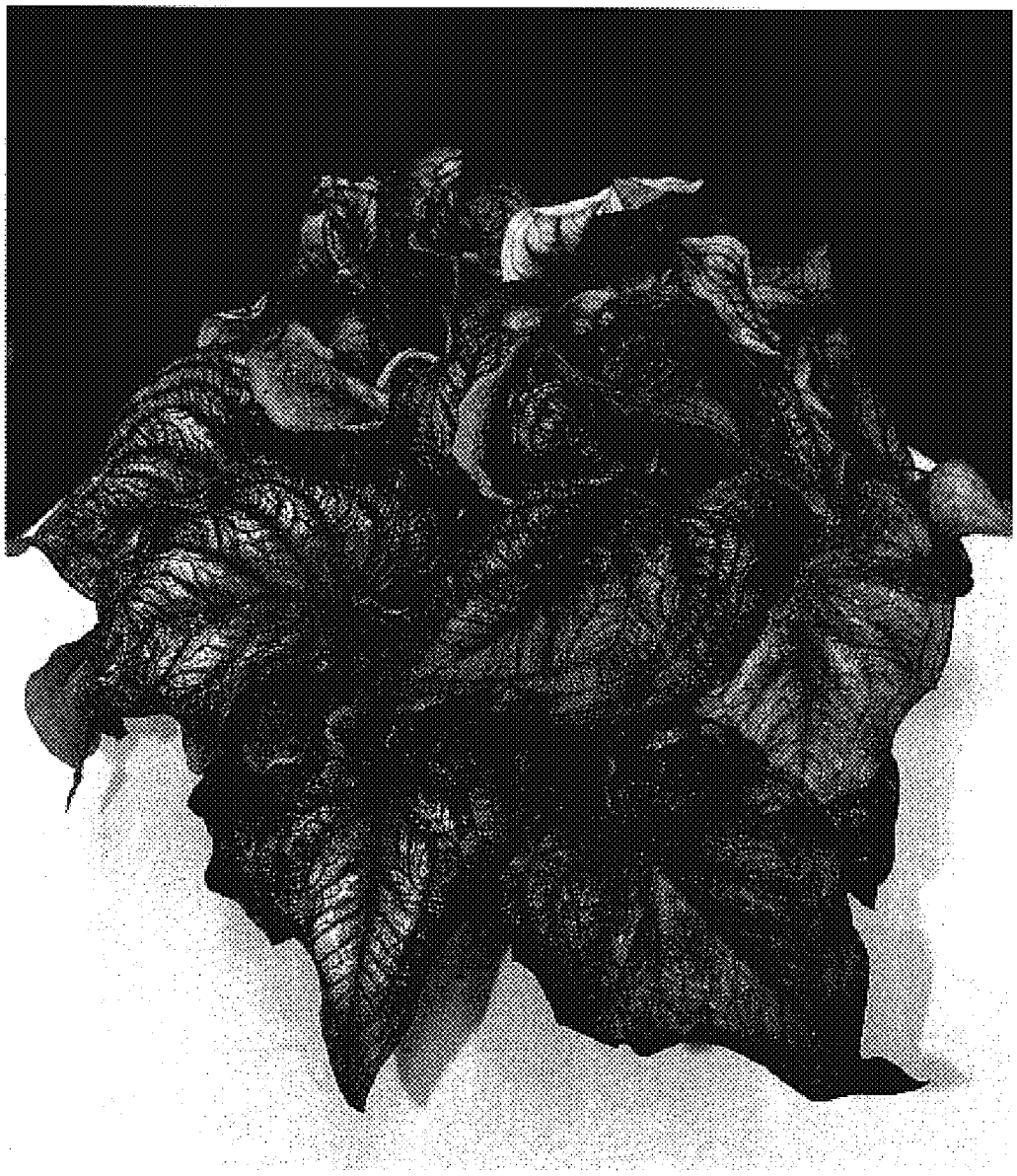

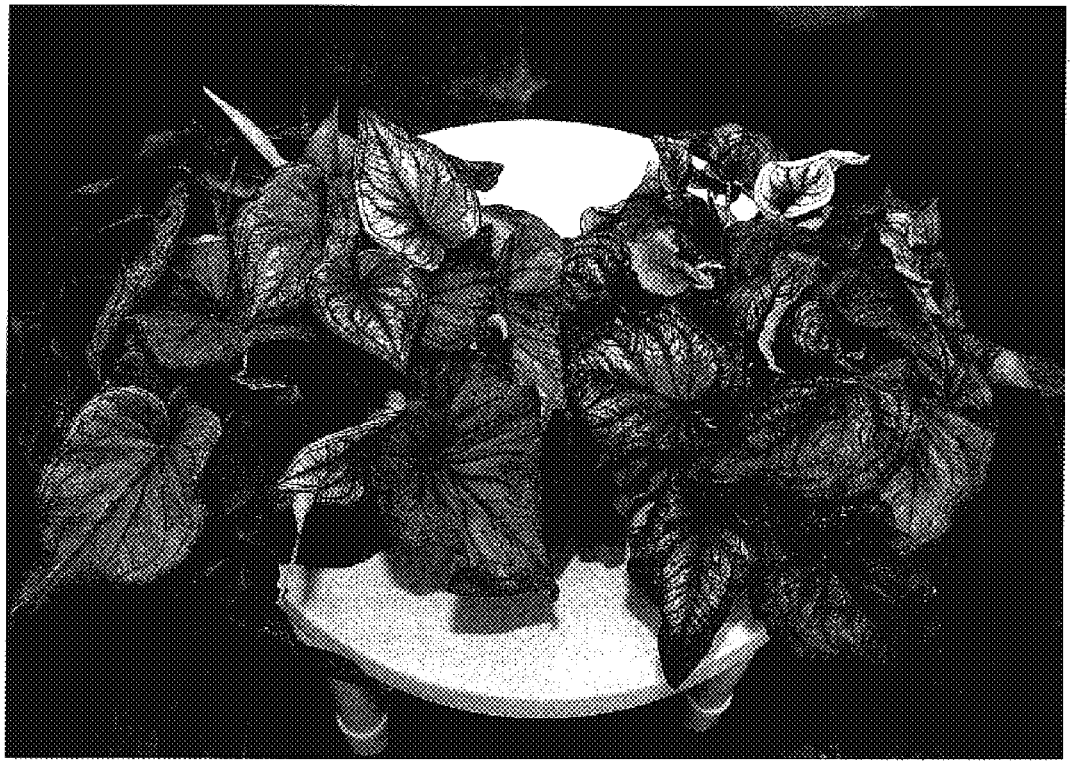

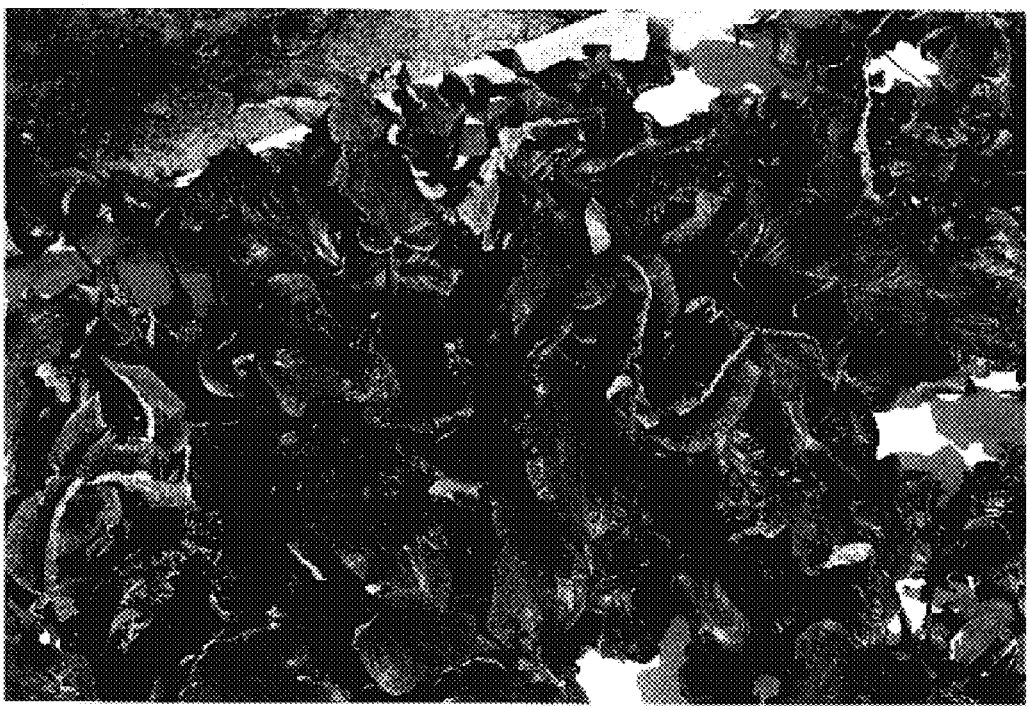
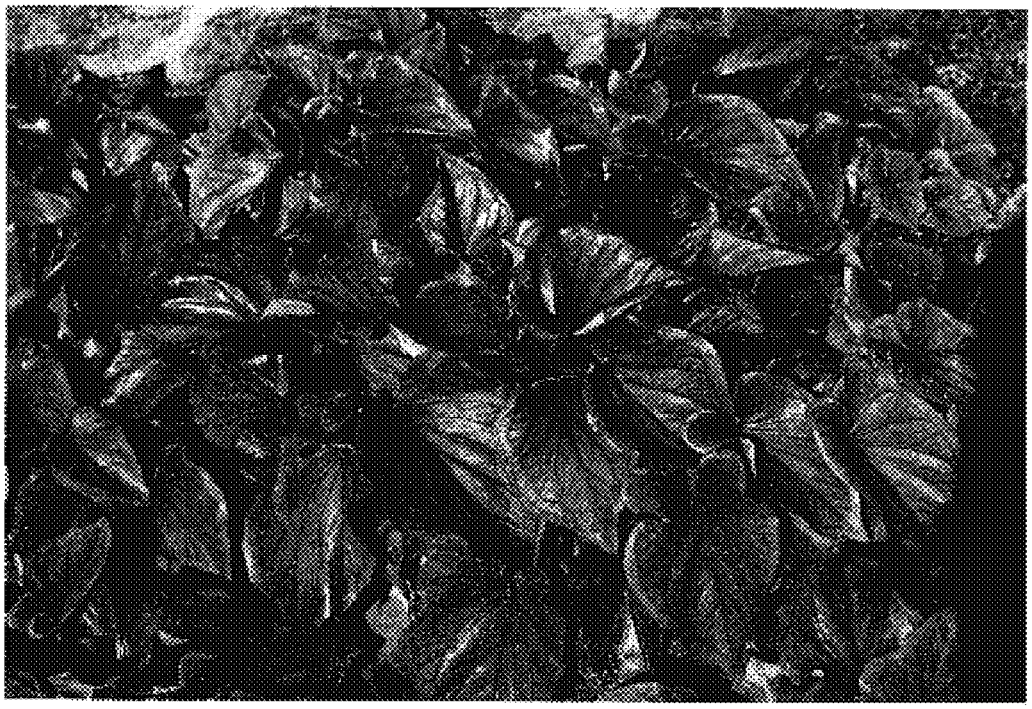

* * * * *